United States Patent [19]

Jones

[11] 4,202,797

[45] May 13, 1980

[54] RECOVERING CATALYST VALUES IN REACTION LIQUORS FROM OXIDATIVE PRODUCTION OF CARBOXYLIC AND POLYCARBOXILIC ACIDS

[75] Inventor: Peter J. V. Jones, Middlesbrough, England

[73] Assignee: Imperial Chemical Industries Limited, London, England

[21] Appl. No.: 882,206

[22] Filed: Feb. 27, 1978

[30] Foreign Application Priority Data

Apr. 7, 1977 [GB] United Kingdom ............... 14834/77

[51] Int. Cl.² ................... B01J 27/32; B01J 27/28; C07C 51/42; C01G 45/00; C01G 51/00
[52] U.S. Cl. .................................. 252/413; 252/415; 423/49; 423/52; 423/139; 562/414; 562/593
[58] Field of Search ................ 252/413, 415; 260/525; 423/49, 52, 139; 562/414

[56] References Cited

U.S. PATENT DOCUMENTS

| | | | |
|---|---|---|---|
| 2,964,559 | 12/1960 | Burney et al. | 252/525 |
| 3,033,899 | 5/1962 | Knobloch et al. | 260/525 |
| 3,780,096 | 12/1973 | Johnson et al. | 252/413 |
| 4,008,306 | 2/1977 | Yamashita et al. | 252/413 |

FOREIGN PATENT DOCUMENTS

899288 6/1962 United Kingdom ............... 260/525

*Primary Examiner*—P. E. Konopka
*Attorney, Agent, or Firm*—Cushman, Darby & Cushman

[57] ABSTRACT

Heavy metal values are recovered from mother liquors remaining from oxidations to mono- or poly- carboxylic acids in aliphatic monocarboxylic acids in presence of catalyst heavy metals and bromides by (1) concentrating, (2) precipitating and (3) separating heavy metals as sulphates and (4) recovering aliphatic monocarboxylic acid and HBr by distillation, (5) dissolving sulphates in water, (6) adsorbing heavy metals on a cation exchange resin and (7) desorbing them, preferably with the solution from Step 4.

9 Claims, No Drawings

RECOVERING CATALYST VALUES IN REACTION LIQUORS FROM OXIDATIVE PRODUCTION OF CARBOXYLIC AND POLYCARBOXILIC ACIDS

This invention relates to a process for recovering catalyst values, more especially from reaction mixtures resulting from the manufacture of mono or polycarboxylic acids by catalytic liquid phase oxidation with a molecular oxygen-containing gas of feedstocks oxidisable thereto.

The invention provides a process for recovering catalyst values comprising heavy metal ions and bromide ions from the reaction mother liquor resulting from the oxidation in the liquid phase to a mono or polycarboxylic acid of a feedstock oxidisable thereto by means of a molecular oxygen-containing gas in presence of a lower aliphatic monocarboxylic acid and of a catalyst comprising said heavy metal ions and said bromide ions followed by separation of the said mono or polycarboxylic acid from the said reaction mother liquor, which process comprises, (1) concentrating the said reaction mother liquor, if necessary, until the concentration of said heavy metal ions in the concentrate is at least 1000 parts per million (p.p.m.) by weight,
(2) adding sulphuric acid to the said concentrate to precipitate said heavy metal ions as their sulphates,
(3) separating said heavy metal sulphates from the sulphate precipitation mother liquor,
(4) distilling the sulphate precipitation mother liquor to obtain an overhead fraction comprising aliphatic monocarboxylic acid, hydrogen bromide and water, which fraction is condensed to a liquid,
(5) dissolving the precipitated heavy metal sulphates from step 3 in water,
(6) contacting the aqueous heavy metal sulphate solution with a cation exchange resin whereby the heavy metal values are absorbed on said resin and an aqueous solution of sulphuric acid is obtained, and
(7) eluting the heavy metal values from the said cation exchange resin with a solution of hydrogen bromide in said lower aliphatic carboxylic acid.

The heavy metal ions of the catalyst are preferably cobalt or manganese ions or mixtures thereof. Other heavy metal ions which may be used in catalysts, possibly in addition to cobalt and/or manganese ions, for the manufacture of mono or polycarboxylic acids by oxidation of an appropriate feedstock with a molecular oxygen-containing gas and which may be recovered by our process are for example, cerium and zirconium.

Mono or polycarboxylic acids manufactured by catalytic oxidation reactions from which the catalyst values may be recovered by the process of our invention include those resulting from the oxidation of hydro-carbon feedstocks. Particularly suitably hydrocarbon feedstocks are monoalkylbenzenes, for example toluene and ethylbenzene oxidation of which leads to benzoic acid, dialkylbenzenes, for example xylenes, diethylbenzenes and diisopropylbenzenes oxidation of which leads to a phthalic acids, namely o-phthalic acid, isophthalic acid and terephthalic acid according to the orientation of the alkyl substituents in the starting hydrocarbon, and trialkylbenzenes, for example 1, 2, 4-trimethylbenzene oxidation of which leads to trimellitic acid. Other suitable hydrocarbon feedstocks are, for example cyclohexane giving adipic acid on oxidation. Other suitable feedstocks are di(halogenoalkyl)- benzenes, for example di(chloromethyl) benzene, oxidation of which gives phthalic acids, and partially oxygenated derivatives of hydrocarbons, whether these are obtained by partial oxidation of the hydrocarbons themselves or by other methods. Such partially oxygenated derivatives are usually alcohols, aldehydes or ketones, or carboxylic acids, for example methylbenzyl alcohols, tolualdehydes, toluic acids, carboxybenzaldehydes, cyclohexanol and cyclohexanone. Mixtures of such feedstocks may be used.

The lower aliphatic monocarboxylic acid preferably has from 2 to 4 carbon atoms for example acetic acid, propionic acid and butyric acid. Acetic acid is especially preferred.

The mono or polycarboxylic acid product of the oxidation reaction is separated from the reaction mother liquor usually by filtration of centrifuging. The carboxylic acids are usually solids relatively poorly soluble in the lower aliphatic monocarboxylic acid except at elevated temperatures, and separation of the carboxylic acid may be assisted by cooling the reaction mixture and/or by distilling off lower aliphatic mono-carboxylic acid and/or water prior to separation. The mother liquor contains, in addition to the lower aliphatic monocarboxylic acid and catalyst values, other ions which may be introduced incidentally to the introduction of heavy metal ions and/or bromide ions, water which is formed in the oxidation reaction and which may be incompletely removed during the reaction and any preliminary treatment, organic impurities, for example small amounts of carboxylic acid oxidation product, incompletely oxidised material and by products, and metallic impurities especially traces of metals removed from the structure of the manufacturing plant by corrosion, for example iron, chromium or nickel. Ions introduced incidentally may, for example, be alkali metal, especially sodium ions, where, for example the bromide ion is introduced as sodium bromide or where for example, caustic alkalis are used in the plant for washing purposes and small amounts are transferred to the mother liquor.

In step 1 of our recovery process the reaction mother liquor is concentrated, if necessary, until the concentration of heavy metal ions is at least 1000 ppm by weight since the recovery process is uneconomic at much lower concentrations. Preferably the concentration is at least 5000 ppm and more preferably 10,000 ppm (1%) by weight and is conveniently in the range 1% to 5% by weight. Concentration is conveniently effected by distillation and at the same time an overhead fraction is obtained comprising lower aliphatic monocarboxylic acid and water in so far as water is present in the mother liquor. The proportion of overhead fraction obtained from the mother liquor depends on the degree of concentration it is desired to effect in the heavy metal ions in the mother liquor which depends on the absolute amounts present there initially. The lower aliphatic monocarboxylic acid so recovered may be re-used in the oxidation process.

In step 2 of our recovery process sulphuric acid is added to the mother liquor, after concentration, if necessary, in step 1, to precipitate the heavy metal ions as their sulphates. Precipitation is conveniently carried out hot, for example at temperatures from 70° to 115° C., since it may then be unnecessary to cool the concentrate after distillation, and separation of some unwanted materials, for example some organic impurities, with the sulphates may be avoided. The amount of sulphuric acid used in the approximate molar equivalent of the heavy metal ions present, and there is generally no advantage in using much in excess of the molar equivalent although it is preferred to have a slight excess of free sulphuric acid to ensure complete precipitation. The sulphuric acid may be added in concentrated form or more conveniently as an aqueous solution, for example a 10% to 50% by weight aqueous solution. Owing to the solubility of the heavy metal sulphates in water the use of very dilute aqueous solutions of sulphuric acid is to be avoided. Thus we prefer that, by adjusting the water level in the concentration process of step 1 and by controlling the amount of water added with the sulphuric acid in step 2, the amount of water in the sulphate precipitation mother liquor is less than 20% by weight. Further, since (as set out below) we prefer in the elution step 7 of our process to control the level of water in the eluting solution to 3 to 10%, we particularly prefer in this sulphate precipitation step to control the level of water to these same values.

In step 3 of our recovery process the heavy metal sulphates are separated from the sulphate precipitation mother liquor. Separation is effected by conventional methods, e.g. by filtration of centrifuging. The sulphate precipitation mother liquor contains bromide ions, alkali metal ions, metal ions produced by plant corrosion an organic impurities dissolved in lower aliphatic carboxylic acid. In step 4 the sulphate precipitation mother liquor is distilled to give an overhead fraction which is condensed, and contains lower aliphatic monocarboxylic acid, hydrogen bromide and water. The bromide ion catalyst values are thus recovered. The bottoms fraction containing the unwanted materials is disposed of to waste.

In step 5 of our recovery process the precipitated heavy metal sulphates are dissolved in water. The amount of water used is not critical but the concentration of heavy metal ions in the solution is conveniently in the range 0.2% to 10% by weight. Ambient temperatures or temperatures somewhat above ambient are conveniently used for solution, for example temperatures in the range 5° to 50° C.

In step 6 of our recovery process the aqueous solution of heavy metal sulphates is contacted with a cation exchange resin. The latter may be any cation exhange resin, for example a sulphonated polystyrene resin (eg Dowex 50 WX8, Amberlite 2001 or Amberlite 15: the words DOWEX and AMBERLITE are Trade Marks.) Contacting may be effected in any convenient manner, a particularly suitable method being to pass the aqueous solution through a column containing the ion exchange resin. As a result of the contact the heavy metal ions are adsorbed on the resin and sulphuric acid passes out of the column unadsorbed. The sulphuric acid so obtained may be re-used in step 2 of our process to precipitate the heavy metal sulphates. In this way the small proportion of heavy metal ion which leaves the column in solution is retained in the system. If desired, the sulphuric acid may be concentrated before re-use, by evaporating or distilling off water.

In step 7 of our recovery process the heavy metal ions adsorbed in the cation exchange resin are eluted with a solution of hydrogen bromide in the lower aliphatic carboxylic acid and water. Conveniently the solution used for elution is the overhead fraction obtained in the distillation in step 4 of our process, although adjustments to it may be made by adding more lower aliphatic carboxylic acid or more hydrobromic acid. Typically the eluting solution will contain up to 20% by weight of water, and preferably from 3 to 10%, and typically will contain from 1% to 5% by weight of hydrogen bromide dissolved in lower aliphatic carboxylic acid, although the effectiveness of our process is not limited to such porportions. It is preferred to control the water level in the sulphate precipitation step 2 to that required in the elution step 7 since virtually the whole of the water is distilled in the distillation step 4. The elute then comprises a solution of the heavy metal ions and bromide ions in the lower aliphatic carboxylic acid and water, freed from various extraneous ions and organic impurities, and as such is suitable for recycle to the oxidation process for producing the mono or polycarboxylic acid to serve as catalyst in the process, since the extraneous ions and organic impurites which might inhibit that oxidation have been removed. After elution the ion exchange resin is conveniently given a displacement wash with water to remove the remaining lower aliphatic monocarboxylic acid and hydrogen bromide and the wash liquor may also be recycled to the oxidation process. The proportion of heavy metal ion (and where there is more than one heavy metal ion their relative proportion), bromide ion and water in the eluate and/or washings may, if necessary, be adjusted as appropriate to meet the requirements of the oxidation process by adding heavy metal ion, bromide ion or lower aliphatic carboxylic acid. So far as bromide ion is concerned we prefer to add the additional bromide necessary to bring the level up to that required by the oxidation process (since bromide is lost in the off gases in the oxidation) prior to the elution step.

Not all the mother liquor resulting from the manufacture of the mono or poly- carboxylic acid needs to be treated according to the process of our invention. Where the catalyst values are recycled to the oxidation process it will generally be sufficient to treat only a proportion, for example from 10% to 50% by weight, of the mother liquor in order to maintain oxidation-inhibiting impurities in the oxidation reaction mixture at an acceptably low level. The remainder of the mother liquor may be recycled untreated.

The process of our invention is of particular value value for recovering for recycle to the oxidation process cobalt, manganese and bromide catalyst values from the oxidation of p-xylene to terephthalic acid in the presence of a cobalt, manganese and bromide catalyst and an acetic acid solvent.

The invention is illustrated but not limited by the following Examples.

CONCENTRATION (STEP 1)

EXAMPLE 1

The major portion of the mother liquor separated from product terephthalic acid resulting from the air oxidation of p-xylene in the liquid phase in acetic acid in presence of a catalyst comprising cobalt, manganese and bromide ions was recycled to the oxidation. The remainder was distilled to recover part of the acetic acid and to concentrate the catalyst values. The concentrate had the following composition (in parts by million (ppm) by weight unless otherwise stated).

| Na | Cr | Mn | Fe | Co | Ni | Br | H₂O |
|---|---|---|---|---|---|---|---|
| 2525 | 39 | 1265 | 200 | 11665 | 42 | 9400 | 0.5% |

PRECIPITATION (STEP 2) AND SEPARATION (STEP 3)

(EXAMPLE 2-4

To 500 g of the concentrate obtained in Example 1 there was added at 20° C. aqueous sulphuric acid of the composition indicated in the following Table I. The precipitated cobalt and manganese sulphates were filtered off and the filtrate was found to be of the amount and to have the composition indicated in Table 1. From these values the percentage recovery of cobalt and manganese is calculated.

TABLE I

| | | Example 2 | Example 3 | Example 4 |
|---|---|---|---|---|
| Sulphuric Acid | $H_2SO_4$ g | 11.9 | 11.9 | 11.9 |
| Composition | $H_2O$ g | 133.6 | 23.5 | 226.1 |
| Filtrate Amount | g | 615 | 518 | 720 |
| | Na ppm | 2100 | 2395 | 1750 |
| | Cr ppm | 32 | 32 | 19 |
| Filtrate | Mn ppm | 450 | 195 | 445 |
| | Fe ppm | 165 | 175 | 140 |
| Composition | Co ppm | 475 | 815 | 895 |
| | Ni | 1.5 | 4 | 3.5 |
| | Br ppm | 775 | 8900 | — |
| | $H_2O$ % | 20 | 5 | 31 |
| Recovery of | Co % | 95 | 94 | 89 |
| Heavy metals | Mn % | 56 | 86 | 47 |

DISTILLATION (STEP 4)

EXAMPLES 5-6

The filtrates from Examples 2 and 3 were distilled to leave a residue of organic and metallic contaminants. Hydrogen bromide was added to the distillates to make the level suitable for recycle to the oxidation (and thus to compensate for that lost in the oxidation off gases). This gave the quantity of solution having the composition by weight indicated in the following Table II.

TABLE II

| | | Example 5 | Example 6 |
|---|---|---|---|
| Filtrate distilled | | from Ex. 2 | from Ex. 3 |
| Final solution: weight | g | 625 | 518 |
| Composition | | | |
| H Br | wt % | 5 | 5 |
| $H_2O$ | wt % | 20 | 5 |
| Acetic acid | wt % | 75 | 90 |

DISSOLUTION (STEP 5) AND ADSORPTION (STEP 6)

EXAMPLES 7-8

The precipitated cobalt and manganese sulphates obtained in Example 2 were dissolved in water at 20° C. to give a solution of the concentration of cobalt indicated in the following Table III. The solution was pumped at the rate indicated in the Table on to a column containing 200 ml of Amberlite 200 resin until a breakthrough of cobalt ions was indicated by visual inspection. The concentration of the sulphuric acid in the eluant was measured and the % recovery acid calculated. The capacity of the resin for cobalt was also calculated. The results are given in Table III.

TABLE III

| | | Example 7 | Example 8 |
|---|---|---|---|
| Concentration of cobalt sulphate solution | molar | 1.01 | 0.17 |
| Rate of application to column | ml/hr | 250 | 2000 |
| Concentration of $H_2SO_4$ in eluant | % wt. | 8.9 | 1.6 |
| Recovery of $H_2SO_4$ | mole % | 94 | 74 |
| Capacity of resin for cobalt | milli-equivs /ml | 1.7 | 1.6 |

The sulphuric acid from Example 7 was used without distillation for precipitating the heavy metal sulphates as in Example 2. That from Example 8 was concentrated by distillation before such use.

DESORPTION (STEP 7)

EXAMPLES 9, 10 & 11

The solutions obtained as in Examples 5 and 6 were poured through a 200 ml bed of a strong acid ion exchange resin saturated with cobalt at the rate and for the time indicated in Table IV. The amount of cobalt eluted was measured and this is expressed as a percentage of the amount precipitated in Example 2.

TABLE IV

| | | Example 9 | Example 10 | Example 11 |
|---|---|---|---|---|
| Origin of Eluant Solution | | from Ex. 5 | from Ex. 5 | from Ex. 6 |
| Rate of application to column | ml/hr | 250 | 500 | 250 |
| Time of application to column | mins. | 150 | 75 | 124 |
| Weight of cobalt eluted | g. | 4.93 | 3.31 | 6.68 |
| Cobalt eluted as % of that precipitated in Example 2 | | 90 | 60 | >100 |

The following Examples illustrate the preferred method of operating the resin column.

ADSORPTION (STEP 6)

EXAMPLES 12 AND 13

An aqueous solution of cobalt sulphate of the concentration given in Table V and obtained as described in Examples 7 and 8 was pumped upwards through the resin indicated in the table at the rate there indicated until a breakthrough of cobalt ions was indicated by visual inspection. The capacity of the resin for cobalt was calculated and is given in the table. The resin was then given a displacement wash with di-ionised water in an upwards direction at a rate of 3 bed-volumes per hour, and then an acetic acid wash with 95% by weight aqueous acetic acid at a rate of 2 bed-volume per hour, also in an upwards direction.

DESORPTION (STEP 7)

EXAMPLES 14 AND 15

The eluant solution consisting of acetic acid containing water and hydrobromic acid as indicated in Table VI was passed downwards through the resin at the rate indicated in the table. The amount of cobalt eluted for a specified volume eluant is indicated in the table. The resin was then given an acetic acid wash with 95% by weight aqueous acetic acid at a rate of 1 bed-volume per hour and then a rinse with de-ionised water at a rate of 2 bed-volumes per hour, both in a downwards direction. The cycle was then repeated, starting with further adsorption of cobalt from aqueous cobalt sulphate solution.

TABLE V

| | | Example 12 | Example 13 |
|---|---|---|---|
| Concentration of cobalt sulphate solution | molar | 0.07 | 0.07 |
| Resin | | Amberlite 15 (H form) | Amberlite 200 (H form) |
| Rate of application to column | ml/hr bed-volumes per hour. | 2078 3 | 2100 3 |
| Capacity of resin for cobalt | milli-equivs per ml | 1.72 | 1.62 |

TABLE VI

| | | Example 14 | Example 15 |
|---|---|---|---|
| Composition of Eluant Solution | | | |
| Water | % wt | 4.8 | 7.2 |
| HBr | % wt | 4.1 | 4.1 |
| Rate of Application to column | ml/hr bed-volumes per hour | 350 0.5 | 700 1.0 |
| Volume of Eluant used | ml | 1750 | 1750 |
| Wt. of Cobalt Eluted | g. | 17.00 | 16.59 |

I claim:

1. A process for recovering catalyst values comprising heavy metal ions and bromide ions from the reaction mother liquor resulting from the oxidation in the liquid phase to a mono aromatic carboxylic acid product or a polycarboxylic acid product of a feedstock oxidisable thereto by means of a molecular oxygen-containing gas in presence of a lower aliphatic monocarboxylic acid and of a catalyst comprising said heavy metal ions and said bromide ions followed by separation of the same mono or polycarboxylic acid product from the said reaction mother liquor, which process comprises, (1) concentrating the said reaction mother liquor, when necessary, until the concentration of said heavy metal ions in the concentrate is at least 1000 parts per million (p.p.m.) by weight, (2) adding sulphuric acid to the said concentrate to precipitate said heavy metal ions as their sulphates, (3) separating said heavy metal sulphates from the sulphate precipitation mother liquor, (4) distilling the sulphate precipitation mother liquor to obtain an overhead fraction comprising lower aliphatic monocarboxylic acid, hydrogen bromide and water, which fraction is condensed to a liquid, (5) dissolving the precipitated heavy metal sulphates from step 3 in water, (6) contacting the aqueous heavy metal sulphate solution with a cation exchange resin whereby the heavy metal values are absorbed on said resin and an aqueous solution of sulphuric acid is obtained, and (7) eluting the heavy metal values from the said cation exchange resin with a solution of hydrogen bromide in said lower aliphatic carboxylic acid recovered from step 4.

2. The process of claim 1 in which the heavy metal ions are cobalt or manganese ions or mixtures thereof.

3. The process of claim 1 in which the reaction liquor results from the oxidation of p-xylene to terephthalic acid.

4. The process of claim 1 in which the sulphuric acid obtained in step 6 is re-used in step 2.

5. The process of claim 1 in which the eluting solution in step 7 contains from 3% to 10% by weight of water.

6. The process of claim 1 in which the elute from step 7 is recycled to the oxidation process for producing the mono aromatic carboxylic acid product or polycarboxylic acid product to serve as catalyst in the process.

7. The process of claim 6 in which the proportion of heavy metal ion, bromide ion and/or water in the eluate is adjusted, prior to recycle, to that required by the oxidation process.

8. The process of claim 7 in which any additional bromide ion required is added to the eluting solution for step 7 prior to the elution step.

9. The process of claim 1 in which from 10% to 50% by weight of the reaction mother liquor resulting from the oxidation is treated for recovering catalyst values.

* * * * *